(12) United States Patent
Hillbratt (10) Patent No.: US 10,195,432 B2
(45) Date of Patent: Feb. 5, 2019

(54) SYSTEMS AND METHODS FOR NON-OBTRUSIVE ADJUSTMENT OF AUDITORY PROSTHESES

(71) Applicant: COCHLEAR LIMITED, Macquarie University (AU)

(72) Inventor: Martin Evert Gustaf Hillbratt, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 25 days.

(21) Appl. No.: 14/947,900

(22) Filed: Nov. 20, 2015

(65) Prior Publication Data

US 2016/0144178 A1 May 26, 2016

Related U.S. Application Data

(60) Provisional application No. 62/083,065, filed on Nov. 21, 2014.

(51) Int. Cl.
*A61N 1/00* (2006.01)
*A61N 1/36* (2006.01)

(52) U.S. Cl.
CPC ..... *A61N 1/36032* (2013.01); *A61N 1/36036* (2017.08)

(58) Field of Classification Search
CPC .................................................. A61N 1/36032
USPC ........................................................... 607/57
See application file for complete search history.

(56) References Cited

U.S. PATENT DOCUMENTS

2015/0216414 A1* 8/2015 Wood ....................... G09B 7/00
600/303

* cited by examiner

*Primary Examiner* — Nadia A Mahmood
(74) *Attorney, Agent, or Firm* — Merchant & Gould P.C.

(57) ABSTRACT

Systems and methods for performing non-obtrusive, automatic adjustment of an auditory prosthesis are disclosed. A control expression can be detected during a conversation. Upon detection of the control expression, an audio setting adjustment can be selected and applied to the auditory prosthesis. Multiple adjustments can be made in response to identifying multiple control expressions during a conversation.

20 Claims, 7 Drawing Sheets

SYSTEMS AND METHODS FOR NON-OBTRUSIVE ADJUSTMENT OF AUDITORY PROSTHESES

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because some or all of the hair cells in the cochlea functional normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and may be suitable for individuals who cannot derive sufficient benefit from conventional hearing aids.

SUMMARY

Embodiments disclosed herein relate to systems and methods for performing non-obtrusive, automatic adjustment of an auditory prosthesis. In embodiments, a control expression can be detected during a conversation. Upon detecting the control expression, an audio setting adjustment can be selected and applied to the auditory prosthesis. The embodiments disclosed herein further provide for performing multiple adjustments in response to identifying multiple control expressions during a conversation.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Many recipients of auditory prostheses have problems useful sounds in some sound environments. For example, when in an environment with a significant number of discrete and 10 inputs (e.g., multiple conversations at a cocktail party), it can be very difficult for a recipient to differentiate their conversation from those around them. Different recipients can also have different hearing difficulties in different environments. For example, one recipient can hear well in a first environment (e.g., a cocktail party), but poorly in a different environment (e.g., a sports arena). Thus, it can be difficult for a manufacturer of a hearing device, auditory prosthesis, or mobile phone to predict in exactly which situation hearing is difficult for a particular recipient. To address this, a recipient could adjust the settings on their device to improve performance, but can be anxious to do so in a social situation. Such adjustments might require the recipient to nod or tap their device to control its operation. This behavior can be observed by others as odd. Indeed, in the context of auditory prostheses, recipients are often more sensitive about "fitting in" with others and do not want to draw attention to their use of such a device. In addition, recipients with totally implanted devices might not have the ability to change settings on an external part without using a remote controller.

A control process that can be used to adjust the output from an auditory prosthesis is described in this specification. Embodiments of the process facilitate discreet setting adjustments by the recipient of an auditory prosthesis without the use of conventional hardware interfaces (such as dials or buttons). An auditory control system affiliated with the auditory prosthesis monitors the recipient's conversations and adjusts sound processing settings when the control system determines that the current output from the auditory prosthesis is inadequate. The general process can be applied to implanted auditory prostheses and other devices (including non-auditory devices). Some exemplary applications and alternate embodiments are outlined later in the specification.

The auditory prosthesis control system can classify conversational dialog in two categories: recipient contributions and non-recipient contributions. The auditory control system evaluates recipient contributions for indicators of inadequate audio stimulation. Contributions that are determined to originate from another party involved in the conversation are usually discarded by the control system (i.e. the control system is typically not responsive to non-recipient contributions). Dialog classification can be assisted by existing auditory prosthesis components (such as an implanted microphone) and/or new components (such recipient voice recognition systems in a sound processor or ancillary device). The auditory prosthesis can leverage ancillary computing systems (such as a smart phone or body worn accessory) to facilitate speech recognition and other processing detailed herein.

The auditory control system detects natural language indicators used by the recipient during conversational dialog that are indicative of compromised hearing. The indicators are usually designated control expressions that perform dual functions in that they indicate to the auditory control system that the auditory output is inadequate for the current environment, and they form a contribution to an ongoing conversation. The control expressions are typically selected from phrases used in common parlance to indicate difficulty hearing, such as "excuse me?", "pardon me?", "please repeat that". Other parties involved in the conversation would not necessarily know that the recipient is simultaneously issuing a command to the recipient's auditory prosthesis and participating in the conversation.

The auditory control system uses a speech processor to evaluate the recipient's dialog and detect designated control expressions that form part of an ongoing conversation. This process is typically performed without intervention from the recipient (i.e. the recipient does not need to use a conventional interface, such as a button or dial, to initiate speech recognition). The speech processor uses a speech recognition algorithm to differentiate affirmative use of control expressions from dialog that incidentally includes control expressions. For example, the control expression "what" can indicate that the recipient is experiencing difficulty hearing, or form part of a wider dialog (such as "what did you have for dinner?") that is not intended to be a control expression to the auditory prosthesis.

As indicated above, many auditory prosthesis recipients have problems differentiating desirable sounds from undesirable sounds in some sound environments. These problems can be addressed, for example, by noise reduction management, a compressor system to give the best amplification for signals with loudness close to normal speech, beam forming, and other modifications to stimulation output, sound processing, etc. Also, a sound environment can be classified by the device (for example, as the recipient enters a new environment or the existing environment changes). Such a classification can activate different features of the prosthesis so as to optimize sound processing and stimulation based on preset criteria. Still, there are situations where a recipient does not hear what is said or what she wants to hear. As described above, real-time adjustment of the auditory prosthesis can be awkward for a recipient, so much in fact that the recipient can choose to forego better available performance so as not to draw attention to her use of a prosthesis.

Embodiments of the proposed technology contemplate a device (e.g., an auditory prosthesis, mobile phone, etc.) that detects when the recipient utilizes certain control expressions and automatically adjusts one or more settings based on the detected control expression. In a particular embodiment, the control expression can be a natural language expression such as, for example, a word, phrase, or sound spoken in a typical conversation, which would otherwise indicate that the recipient is having a difficult time hearing a speaker. By saying "what?", "come again?", "huh?", or "could you repeat that?", for example, the device automatically adjusts one or more settings (sound processing, stimulation output, or otherwise) of the device automatically. Other similar control expressions, parts of interrogative pronomen, as well as control expressions in a variety of languages, can also be detected. By focusing on control expressions that are also characterized as typical speech expressions, the recipient can ask for parts of a conversation to be repeated or participants in the conversation to speak up, while simultaneously commanding the device to make adjustments to settings, without drawing attention to herself as a user of the device, e.g., as a recipient of an auditory prosthesis.

In one implementation, the device can recognize such control expressions by a speech recognition feature. Such a feature can detect syllables or portions of speech using a hidden Markov model or other models. Other speech detection methods can be utilized. Speech recognition and/or other speech detection processing is typically activated by the device without direct intervention from the recipient via a conventional hardware interface. The device can automatically match speech processing capabilities to the recipient's sound environment by adjusting parameters of the speech processing algorithms used to detect control expressions. The parameter adjustments can be derived from environmental classifications (used in some hearing prostheses to refine sound processing) and/or other usage characteristics. For example, the device can increase the sampling rate used for speech detection when the recipient is talking or the environmental classification is "speech", reduce the sampling rate when the device determines the recipient has not spoken for a defined time interval, and/or temporarily deactivate speech detection when the environmental classification is "quiet". This reduces power and processing overheads when the device determines that intensive speech processing is not needed.

The device can perform other functionality, such as detecting changes in frequency content within a wording of a phrase such as, for example, changes to the detected formants of speech and/or other changes of frequency response/spectra. Such functionality allows the device to detect how the frequency content changes within spoken wording. This enables the device to detect the difference between, as example, "what" as part of a question and "what" as an expression of a hearing difficulty. That is, the device can detect the so-called "melody of speech" that typically accompanies inquiries and recognize that such inquiries are unrelated to control expressions. In another example, the device can detect the frequency components from surrounding words occurring within a defined time frame and compare these frequency components with the control expression. Thus, minor variations in a control expressions (e.g., "what was that you said?" versus "what was that?") can be detected and acted upon by the device. Other methods can be considered, for example, by detecting the time in between word occurrence. The device can also utilize on-board sensors (vibration, sound, etc.) to ensure that the control expression is coming from the recipient and not a different speaker.

When such a control expression is detected, the device can change any number of settings to adjust the output received by the recipient. For an advanced recipient, certain settings adjusted can be associated with different control expressions. For example, "what was that?" can be associated with loudness for the frequency currently having the best or worst signal to noise ratio, while "could you repeat that?" can be associated with changing the width of a beam former. Repetition of the same control expression in certain embodiments can result in successive changes to the same setting. After changing settings, the device can continue to detect control expressions, certain of which can be used to undo a previous setting change. The recipient can also utilize certain control expressions after a setting change so as to identify a preferred setting change. For example, saying "I understand you", or other control expression, can be detected by the device as a preference by the user for the particular setting change that was made. Alternatively or additionally, the device can undo one or more audio setting changes based on the passage of time or an action of the recipient in relation to defined periods of time. For example, the device can reverse speech setting adjustments (such as reverting from beamforming) when (a) a defined period of time after issuance of the control expression passes, (b) a defined period of quiet time (e.g., a period of time with no dialog after issuance of the control expression), or (c) the recipient interacts with controls of the prosthesis within a relatively short period of time after issuance of the control expression passes (e.g., 10 seconds), but not if the recipient interacts with the controls within a relatively long period of time (e.g., 30 seconds).

The device can associate control expressions issued by the recipient to recent changes in the recipient's sound environment. This facilitates automatic readjustment of audio settings when a disturbance is removed. For example, the device can revert to a previous setting state after detecting a sustained reduction in the level of background noise (such as music or traffic noise). An absence of a previously-detected background noise can initiate a similar reversion. The device is also capable of applying setting adjustments derived from the recipient's control expressions to discrete sound sources in the local sound environment (such as a soft talker or sustained background noise). For example, the device can identify the source of individual contributions to a conversation (typically using speech formants or the directionality of the source) and adjust the audio settings for sound originating from a designated participant responsive to an associated control expression. The device can use discrete audio setting adjustments to refine the overall sound environment (such as by reducing the perceived volume of neighboring conversations) and/or enhance discrete sound components (such as increasing the gain used for a softly-spoken conversation participant).

Figure 1:
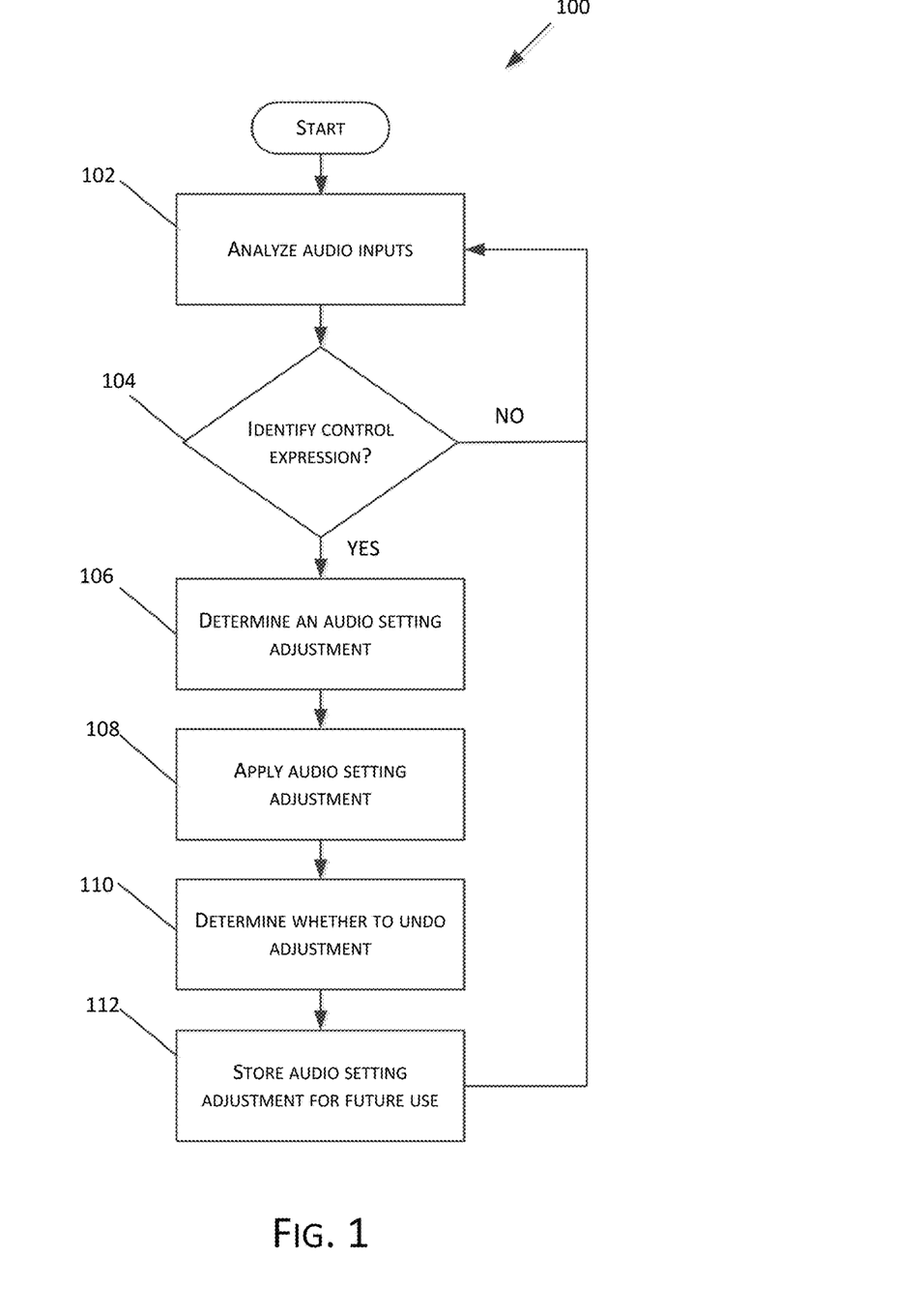
FIG. 1 is an exemplary embodiment of a method for detecting a control expression spoken during conversation and, in response, adjusting the audio settings of an auditory prosthesis.

FIG. 1 is an exemplary embodiment of a method 100 for detecting a control expression spoken during conversation and, in response, adjusting the audio settings of an auditory prosthesis. The method 100 can be implemented using hardware, software, or a combination of hardware and software, such as the hardware and software described herein in relation to FIGS. 4-7. Accordingly, the method 100 can be performed by an auditory prosthesis, a device (e.g., a smartphone) in communication with an auditory prosthesis, or a combination of devices and/or auditory prostheses. For example, an auditory prosthesis with limited charge and/or processing power can leverage a device without such limitations that comes with speech recognition software to perform one or more of the operations described with respect to FIG. 1.

Flow begins at operation 102 where a conversation is analyzed. In embodiments, analyzing a conversation includes analyzing audio input and identifying the start and end of a conversation, which will include speech by the recipient and by another person. The audio input can be words or phrases that humans use to communicate with each other. In embodiments, analyzing the conversation includes identifying at least two speakers engaged in the conversation. Furthermore, analyzing the conversation can include identifying which words and phrases are spoken by a recipient of an auditory prosthesis. In still other embodiments, analyzing the conversation can include identifying information about the environment in which the conversation is taking place or identifying and categorizing multiple sound inputs as conversation, ambient noise, transient environmental conditions (e.g., a siren), etc. For example, operation 102 can include:

- collecting information about ambient noise, background noise, and other data related to environmental characteristics or stimuli;
- performing operations, such as identifying the presence of wind, identifying the presence of additional speakers and/or the loudness of surrounding speech, autocorrelation of the environment, identifying tonality, performing logPowerSpectrum, identifying spectral jaggedness, detecting distortion, timbre, duration of sounds, phase of sounds, and/or signal to noise ratio (SNR), determining a zero-crossing rate, and/or determining a minima/maxima of periodogram;
- analyzing sound related to tonotopy, diachronic change of speech, and/or content of phonemes;
- comparing sound environment properties with database recordings, inharmonicity, repetition pitch, and/or fundamental frequencies and overtones/harmonics; and/or
- determining a reciprocal of the time interval between events in the sound, speech/sound formants, speech, spectral density, pitch, Spectral Peak distortion, Modulation Depth, crest factor, pure tone content in comparison to noise, and/or any derivatives related to such determinations.

Analyzing the conversation in operation 102 can involve distinct processing operations and/or include recording the conversation for subsequent processing. The recorded information can be used to determine the context in which a control expression was spoken and refine initial audio setting adjustments. For example, the device can adjust basic audio settings (such as bass/treble levels, perceived volume control and noise reduction profile) in real-time or close to real-time responsive to a control expression, and subsequently refine the audio setting adjustment (including more sophisticated adjustments) following substantive processing using a recorded segment of the conversation. The recorded information can also be used to associate the control expression with a change in the recipient's sound environment (such as a soft talker or transient noise) and/or aggressively adjust audio settings in response to repeated directives from the recipient. In embodiments, an entire conversation can be recorded or a portion of a conversation can be recorded (e.g., the last 10 seconds of a conversation can be buffered).

In further embodiments, recording of the conversation can be triggered by detection of a control expression. For example, when a control expression is detected, conversation that took place within a predetermined time frame before and/or after detection of the control expression can be recorded. This functionality can be used by the recipient to discreetly store information (such as a name, address or event). For example, the recipient can use the control expression "what did you say your name is?" to get the other party to repeat their name and have the device record that portion of conversation.

The multiple audio inputs (in the form of conversations, unrelated speech, environmental conditions, transient sounds, etc. are monitored for the presence of a control expression, as depicted in operation 104. A lack of control expression returns the method 100 to analysis 102.

In one embodiment, a control expression is a natural language expression commonly spoken in conversation. In one embodiment, identifying the control expression comprises comparing one or more natural language expressions, or subcomponents of a natural language expression, against a dictionary and/or grammar. The dictionary and/or grammar can include words and phrases that are commonly spoken by a person when the person is having a difficult time hearing a speaker. For example, the dictionary or grammar can include the following words and/or phrases: "what?", "come again?", "huh?", or "could you repeat that?". In other embodiments, the dictionary or grammar can include natural language expressions from other languages. In such embodiments, a control expression is identified when a word and/or phrase from the conversation matches a word and/or phrase included in the dictionary and/or grammar. Furthermore, as previously discussed, the recipient can select and/or define the control expressions that can be identified. For example, the recipient can define additional words or phrases as control expressions that the embodiments disclosed herein can identify and, in response, perform an action. As such, in embodiments, a recipient can define a custom dictionary and/or grammar based upon the recipient's personal expressions. In an alternate embodiment, identification of a control expression can be based upon a context in which the control expression was spoken. Determining the context in which a control expression can eliminate false positives. For example, the control expression "what?" can indicate that a recipient is having difficulty hearing but it can also be completely unrelated to the recipient's ability to hear. The context in which the control expression was spoken can be used to address such ambiguities. In such embodiments, once a control expression is detected, the audio input received before the control expression (e.g., a natural language expression) is compared to the audio input received after the control expression. If the audio input before and after the control expression are the same, e.g., if a second person in the conversation repeated what was said before the control expression was spoken, the control expression can be validated as being related to a recipient's ability to hear.

In further embodiments, identification of a control expression can be performed by detection of the tone voice to determine whether a question (e.g., a control expression) was asked. For example, when a person asks a question, she often increases the pitch and/or frequency of her voice at the end of the question. Additionally, the amplitude at the beginning of a question is often detectably higher at the beginning of a phrase than at the end of a phrase. Additionally, questions in which one person asks another to repeat herself are often short. Thus, identification of a control expression can include detecting a start and end time of a phrase and determining whether or not the phrase was a question based on the length of the phrase. Additional embodiments of identifying a control phrase are described with respect to FIG. 2. While exemplary methods for identifying a control expression are described herein, one of skill in the art will appreciate that any or all of these methods can be employed at operation 104. Furthermore, other methods of identifying a control expression can be employed at operation 104 without departing from the spirit and scope of this disclosure.

Upon identification of the control expression, flow continues to operation 106 where an audio setting adjustment is determined in response to identifying the control expression in operation 104. In one embodiment, one or more adjustments to the audio settings of an auditory prosthesis can be determined at operation 106. The determination of the adjustments can be based on the surrounding environment. Information about the surrounding environment can be collected at operation 102, as previously described, or can be collected at operation 106. In alternate embodiments, the determination of a setting adjustment can be based on a predefined hierarchy of audio setting adjustments. In such embodiments, the predefined hierarchy selected to determine the audio setting adjustment can be selected based upon the surrounding environment, or even be present at the time of manufacture and/or programing. Alternatively, an adjustment hierarchy can be set based on user preferences and/or based on the type of auditory prosthesis. The type of audio setting adjustment can vary depending on the type of auditory prosthesis. As illustrated in FIG. 1, the method 100 can be performed in a continuous loop. As such, multiple audio setting adjustments can be applied if a recipient continues to have difficulty hearing. In such embodiments, the order in which the different audio setting adjustments are made is determined based upon the hierarchy. Furthermore, a predetermined threshold can be defined for each type of audio setting adjustment. For example, a continued increase in gain can result in discomfort for the recipient. As such, a predetermined threshold (e.g., 10-15 decibels) can be defined to prevent an audio setting adjustment that can lead to discomfort. Exemplary audio setting adjustments can include change in volume (gain), adjustment in gain for a frequency that has the best or worst signal to noise ratio currently or at the time the control expression was identified, adjustment to the width of a beam former, selection of a noise reduction algorithm (or a different noise adjustment algorithm), adjustment to the aggressiveness of a noise reduction algorithm, etc. One of skill in the art will appreciate that any type of audio setting adjustment can be determined at operation 106. Additional embodiments related to determination of an audio setting adjustment are further described with respect to FIG. 3.

Upon determining an audio adjustment at operation 106, flow continues to operation 108 where one or more audio setting adjustments are applied to an auditory prosthesis of the recipient. In one embodiment, the method 100 can be performed by a device in communication with the auditory prosthesis. For example, voice recognition software that is commonly included with mobile phones can be leveraged to determine whether or not a control expression was spoken. In such embodiments, applying the one or more auditory setting adjustments can include sending an instruction to the auditory prosthesis from a client device (e.g., a smartphone, a tablet, etc. as described herein in connection with FIGS. 6 and 7) to make the determined audio setting adjustment. As such, an auditory prosthesis with limited resources (e.g., memory, power, processing capability, etc.) can leverage the resources of an external device to automatically adjust the auditory prosthesis. In alternate embodiments, for example, if the method 100 is performed by an auditory prosthesis itself, the auditory prosthesis can directly apply the audio setting adjustment at operation 108. The audio setting adjustment applied at operation 108 can be applied by the auditory prosthesis to generate audio output. One of skill in the art will appreciate that the audio output generated by the auditory prosthesis can vary depending on the type of auditory prosthesis. For example, audio output generated by a traditional hearing aid (e.g., airborne sound waves initiated by a single receiver) is different from audio output generated by a cochlear implant (e.g., electric stimulation of the cochlea delivered by a plurality of contacts). However, the aspects disclosed herein can be employed to adjust audio settings (and thus affect audio output) for any type of auditory prosthesis.

Flow continues to operation 110 where a determination is made as to whether the applied audio setting adjustment should be undone. For example, if the recipient does not like the audio setting adjustment, she can instruct the auditory prosthesis to reverse the audio setting adjustment and return to a prior setting. For example, the recipient can press a button or interact with an interface to the auditory prosthesis that instructs the auditory prosthesis to undo the adjustment. In an alternate embodiment, an audio input can be received that indicate that the adjustment should be undone. For example, the recipient can say "ouch" to indicate that the adjustment should be reversed. In one embodiment, a threshold of time around the adjustment can be set. If the indication to undo the adjustment is received within the predetermined time period, the adjustment can be undone. Conversely, if the instruction is received after the predetermined time period there is a likelihood that the adjustment is appropriate and the instruction has been received in error. As such, in embodiments, the adjustment cannot be undone if the instruction is received outside of the predetermined time period.

If a determination is made to undo the adjustment, the adjustment is undone at operation 110. The audio setting adjustment can be stored at operation 112 for future use, then the method returns to operation 102 to continue analysis of the conversation. In alternate embodiments, information related to undoing of the adjustment can be saved for future use, similar to operation 112 described below. For example, embodiments disclosed herein can use such information in the future when selecting the type of adjustments to apply (e.g., not selecting the adjustments that were previously undone). Furthermore, the information can later be accessed by a hearing care professional or the recipient to analyze which changes made to the device were successful or unsuccessful.

Alternatively, the recipient may say "I heard that!" after application of the setting adjustment. This control expression indicates to the device that the setting adjustment has been effective. In embodiments, if the adjustment is to be maintained flow continues to operation 112. At operation 112, the audio setting adjustments are saved for future use. Again, the audio setting adjustment can be stored along with characteristics about the surrounding environment. By doing so, the next time the characteristics about the surrounding environment are detected, the audio adjustments can be automatically applied. After saving the adjustments, flow returns to operation 102 and the method 100 continues.

One of skill in the art will appreciate that the method 100 can be performed in a continuous loop, which enables automatic adjustment of audio settings throughout the entire duration of the recipient's conversation with others. Additionally, one of skill in the art will appreciate that flow can pass directly from operation 102 or another operation to operation 110 or another operation. In other words, operation 110 might not directly follow operation 104. For instance, if a transient, loud noise (e.g., a bus passing nearby) prevents the recipient from hearing another participant of the conversation speaking, the audio settings adjustment might be undone once the loud noise ends. In such scenarios, the flow might pass directly from operation 102, in which the beginning and end of the transient noise is detected, to operation 110.

Figure 2:
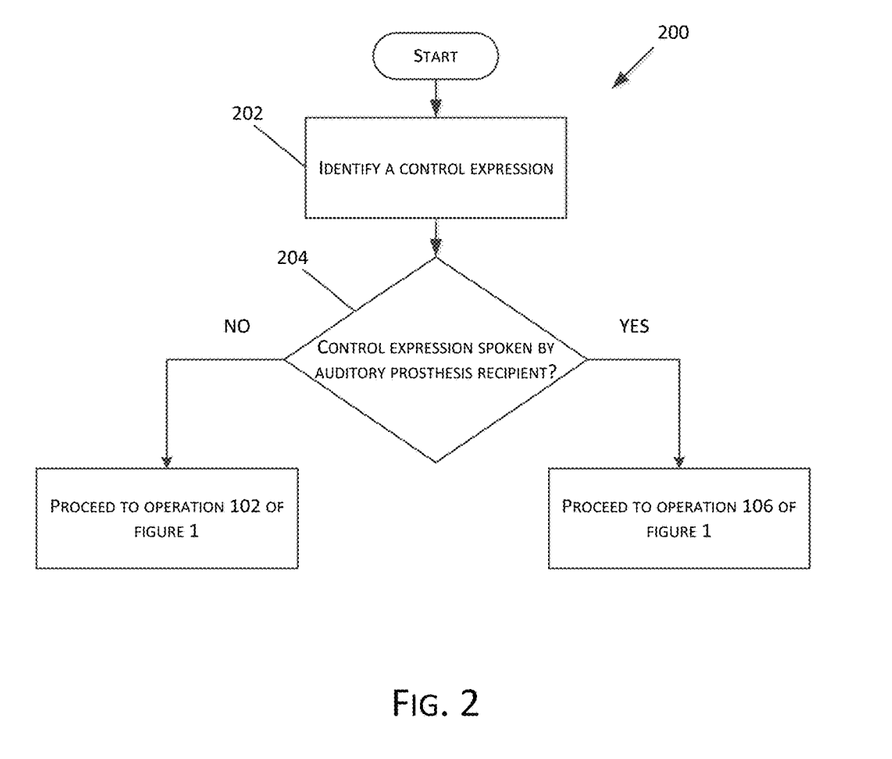
FIG. 2 illustrates an exemplary method 400 of identifying a control expression.

FIG. 2 illustrates an exemplary method 200 of identifying a control expression. The method 200 can be implemented using hardware, software, or a combination of hardware and software. In embodiments, the method 200 can be performed by an auditory prosthesis, a device in communication with an auditory prosthesis, or a combination of devices and/or auditory prostheses. In embodiments, the method 200 can be performed at operation 104 of FIG. 1. The method can be performed in place of or in addition to the different embodiments related to identifying a control expression discussed with respect to operation 104 of FIG. 1. Flow begins at operation 202 where a control expression is identified. The control expression can be identified as described with respect to operation 102 of FIG. 1. In embodiments, upon detection of a control expression, flow continues to operation 204 where a determination is made as to whether or not the control expression is spoken by the recipient of an auditory prosthesis. In one embodiment, the determination can comprise identifying at least two of different speakers in a conversation, where at least one of the identified speakers is the recipient. Identification of the different speakers is helpful to distinguish whether a potential control expression was spoken by the recipient or by another person in the conversation (or in an unrelated, nearby conversation) to ensure that adjustments are applied properly to an auditory prosthesis. For example, if the potential control expression was spoken by another person in the conversation, it is not necessary to make an adjustment to an auditory prosthesis because there is no indication that the recipient is having difficulty hearing. Such a potential control expression is disregarded.

In another embodiment, the determination made at operation 204 can be made based on identification of the recipient. In aspects of such embodiments, the recipient can be identified by associating a vibration with the control expression. For example, if the auditory prosthesis is a bone conduction device, the auditory prosthesis can detect vibrations that are generated by the recipient speaking. Some such devices include a component coupled to the recipient to impart vibrations to the recipient for the purpose of generating the perception of sound. In some such devices, vibrations generated by the recipient, particularly when words are spoken by the recipient, travel through the coupled component to the auditory prosthesis where they are detected and confirm that the recipient spoke. In other auditory prostheses, a subcutaneous microphone is particularly well suited to detect bone conducted vibrations, particularly when words are spoken by the recipient. If the control expression is related to, coincides with, or is otherwise associated with detection of vibrations corresponding to the recipient speaking (e.g., vibrations with amplitude that exceeds a certain threshold) then a determination can be made that the control expression was spoken by the recipient.

In another embodiment, other methods can be employed to determine whether the control expression was spoken by the recipient. For example, multiple microphones can be used to determine the direction of origination of the control expression. If the direction of origination corresponds to a position of the mouth of the recipient, then it can indicate that the recipient spoke the control expression. Additionally, the volume of the control expression can indicate that it was spoken by the recipient (e.g., words spoken by the recipient can be distinctly louder). In yet another embodiment, the determination can be made based on the tone of voice. For example, a device performing the method 200 can be trained to recognize the voice of the recipient, for example, through the recipient reciting natural language expressions during initialization or setup of the device. If the control expression is not spoken by the recipient, flow branches NO and can return to operation 102 of FIG. 1 and the device can continue to analyze the conversation. On the other hand, if the control expression is spoken by the recipient, flow branches YES and can proceed to operation 106 where one or more audio setting adjustments are determined.

Figure 3:
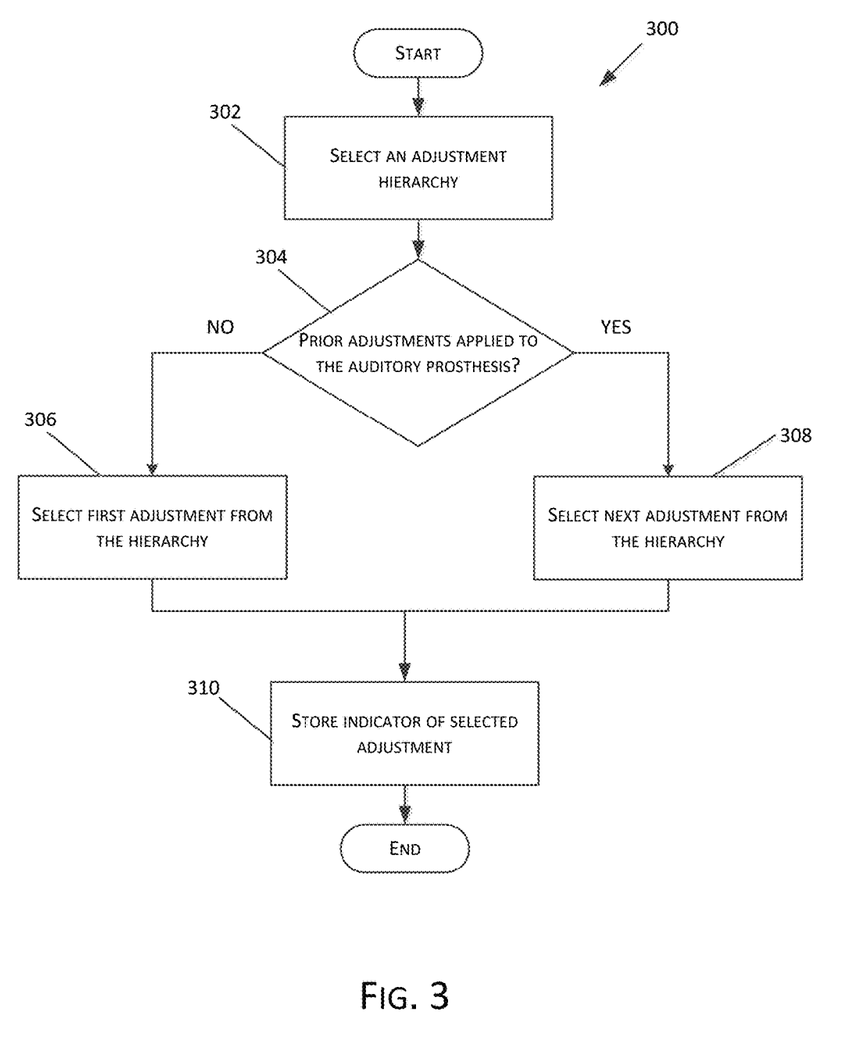
FIG. 3 is an embodiment of an exemplary method 500 for determining an audio setting adjustment.

FIG. 3 is an embodiment of an exemplary method 300 for determining an audio setting adjustment. In embodiments, the method 300 can be performed by an auditory prosthesis, a device in communication with an auditory prosthesis, or a combination of devices and/or auditory prostheses. In embodiments, the method 300 can be performed at operation 106 of FIG. 1. The method can be performed in place of or in addition to the different embodiments related to identifying a control expression discussed with respect to operation 106. Flow begins at operation 302 where an adjustment hierarchy is selected. The adjustment hierarchy can define the types and order of adjustment to automatically apply upon detection of a control expression. In embodiments, multiple adjustment hierarchies can be defined. For example, adjustment hierarchies can be defined based on an environment, based upon the type of auditory prosthesis, and/or based upon user preference. In further embodiments, additional device sensors (e.g., accelerometers, cameras, etc.) can be employed with the embodiments disclosed herein to provide additional information that can be used to determine what type of adjustments should be made. For example, the device can combine the output from an accelerometer with wind noise detection to determine that the recipient is travelling at elevated speed (such as running, cycling, or travelling in an open-top vehicle) and apply an appropriate setting adjustment.

For example, a hearing prosthesis adjustment hierarchy can comprise a combination of the following operations:
  Adjust a noise reduction algorithm or the noise reduction algorithm selection (e.g., a more aggressive noise reduction algorithm such as an impulse and/or single channel noise reduction algorithm).
  Increase amplification.
  Further increase amplification if possible, otherwise decrease non-speech frequencies.
  Increase amplification of speech frequencies (approximately 500 Hz-3 kHz).
  Increase maximum output.
  If utilizing a directionality system, narrow the beam to pick up sounds from a focused sound field or source.
  Perform a speech enhancement algorithm.
  If in a windy environment, apply a wind reduction algorithm.
  Change the environment classification. For example, if the an environmental classifier determines that the environment is a "speech" environment but the recipient still appears to have trouble hearing, then the environment may be reclassified as a different environment (e.g., "speech in noise", "noise, "wind", etc.) and adjustments can be made based upon the new environment classification. Additional embodiments related to the detection and/or classification of environmental characteristics are provided with respect to FIG. 1.
  Based on analysis of the current/past input frequency spectra or decrease other frequencies. For example, based upon prior conversation, the frequency spectra/response changes of a person may be identified and stored. In a noisy environment, the identified frequency spectra and/or response changes may be amplified in order to make it easier to hear the known speaker in a noisy environment. Alternatively, frequency spectra and/or response changes not associated with a known speaker may be turned down.
  Increase gain. For example, apply an aggressive feedback reduction algorithm to match increase of amplification.

While exemplary operations that can be incorporated in adjustment hierarchies are described herein, one of skill in the art will appreciate that other adjustment hierarchy operations can be employed without departing from the spirit or scope of this disclosure. After selecting an adjustment hierarchy, flow continues to decision operation 304 where a determination is made as to whether an adjustment has already been applied to the auditory prosthesis. If not, flow branches NO to operation 306 and the first adjustment setting is selected from the adjustment hierarchy. If an adjustment setting has been previously applied, flow branches and the next adjustment from the adjustment hierarchy is selected to be applied to the auditory prosthesis. Flow continues from both operations 306 and 308 to operation 310. At operation 310, an indicator of the selected adjustment setting selected at either operation 306 or 308 is stored. The indicator can be used to determine whether a prior adjustment has been applied at operation 304 and to select the next adjustment from the adjustment hierarchy at operation 308.

The technologies disclosed herein can be used in conjunction with various types of auditory prostheses, including active transcutaneous bone conduction devices, passive transcutaneous devices, middle ear devices, cochlear implants, and acoustic hearing aids, or other devices acting as an auditory prosthesis. The devices can be wearable (i.e., entirely external to the recipient), partially implanted or totally implantable (either in or on the head, including in specific portions of the anatomy, e.g., in the mouth or below the skin of the skull). Additionally, the technologies can be incorporated into other devices that process sound for a member of a conversation. For example, dual purpose control expressions can be used to, e.g., control the volume of a mobile phone while it is being used "hands-free" (such as while the user is driving). The person the recipient is speaking to would not necessarily be aware that the recipient has used a control expression or that the volume of the mobile phone has been adjusted. The corresponding stimulus generated by the device can be in the form of electrical signals, mechanical vibrations, or acoustical sounds.

Figure 4:
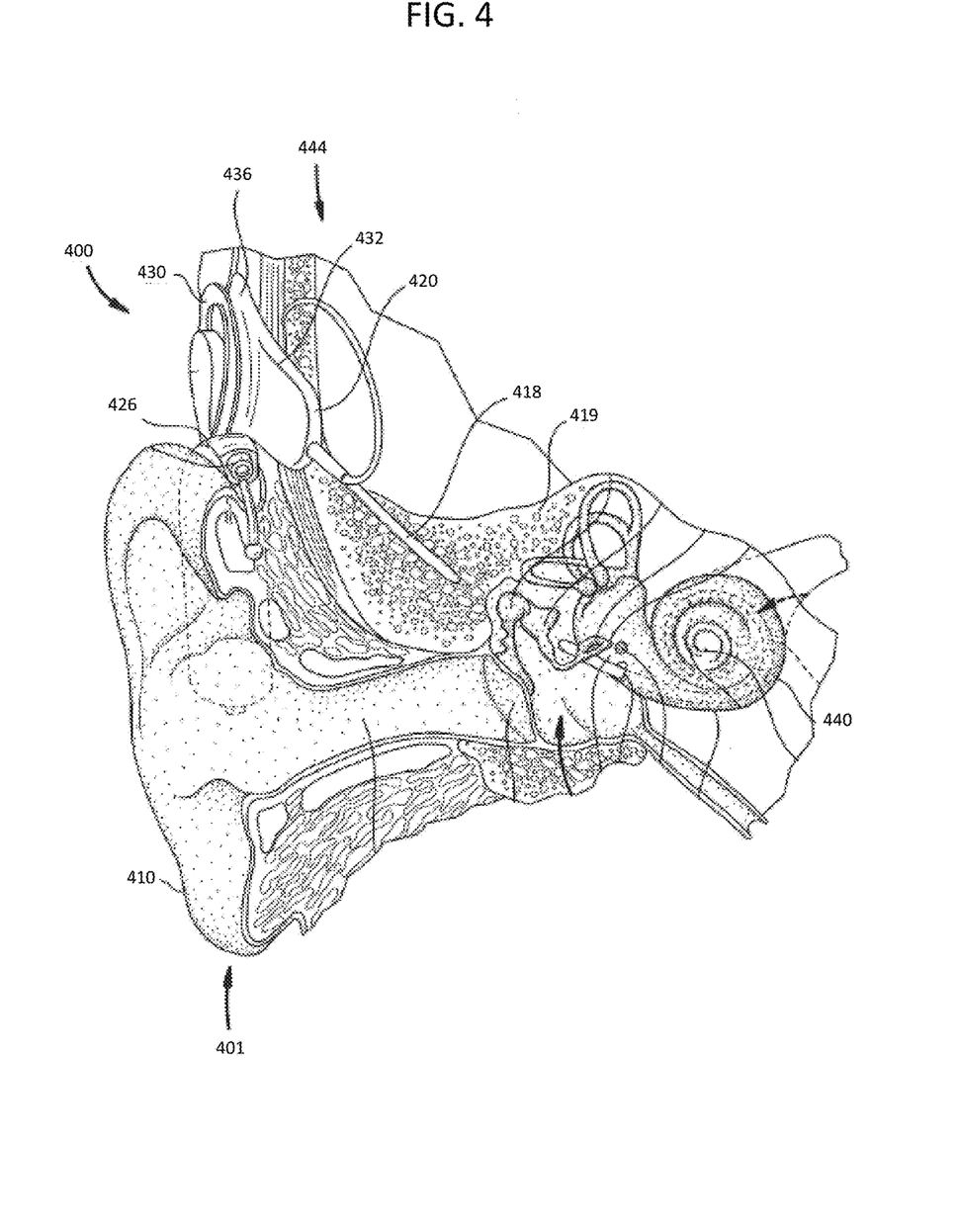
FIG. 4 is a view of a cochlear implant worn on a recipient.

FIG. 4 is a view of a cochlear implant 400 worn by a recipient 401. The cochlear implant 400 includes an internal component 444 typically having an internal receiver/transceiver unit 432, a stimulator unit 420, and an elongate stimulating assembly 418. The internal receiver/transceiver unit 432 permits the cochlear implant 400 to receive and/or transmit signals to an external device 426 and includes an internal coil 436, and preferably, a magnet (not shown) fixed relative to the internal coil 436. Internal receiver unit 432 and stimulator unit 420 are hermetically sealed within a biocompatible housing, sometimes collectively referred to as a stimulator/receiver unit. The magnets facilitate the operational alignment of the external and internal coils, enabling internal coil 436 to receive power and stimulation data from external coil 430. Elongate stimulating assembly 418 has a proximal end connected to stimulator unit 420, and a distal end implanted in cochlea 440. Stimulating assembly 418 extends from stimulator unit 420 to cochlea 440 through mastoid bone 419.

In certain examples, external coil 430 transmits electrical signals (e.g., power and stimulation data) to internal coil 436 via a radio frequency (RF) link, as noted above. Internal coil 436 is typically a wire antenna coil comprised of multiple turns of electrically insulated single-strand or multi-strand platinum or gold wire. The electrical insulation of internal coil 436 is provided by a flexible silicone molding (not shown). In use, implantable receiver unit 432 can be positioned in a recess of the temporal bone adjacent auricle 410 of the recipient. Various types of energy transfer, such as infrared (IR), electromagnetic, capacitive and inductive transfer, can be used to transfer the power and/or data from external device to cochlear implant.

Figure 5:
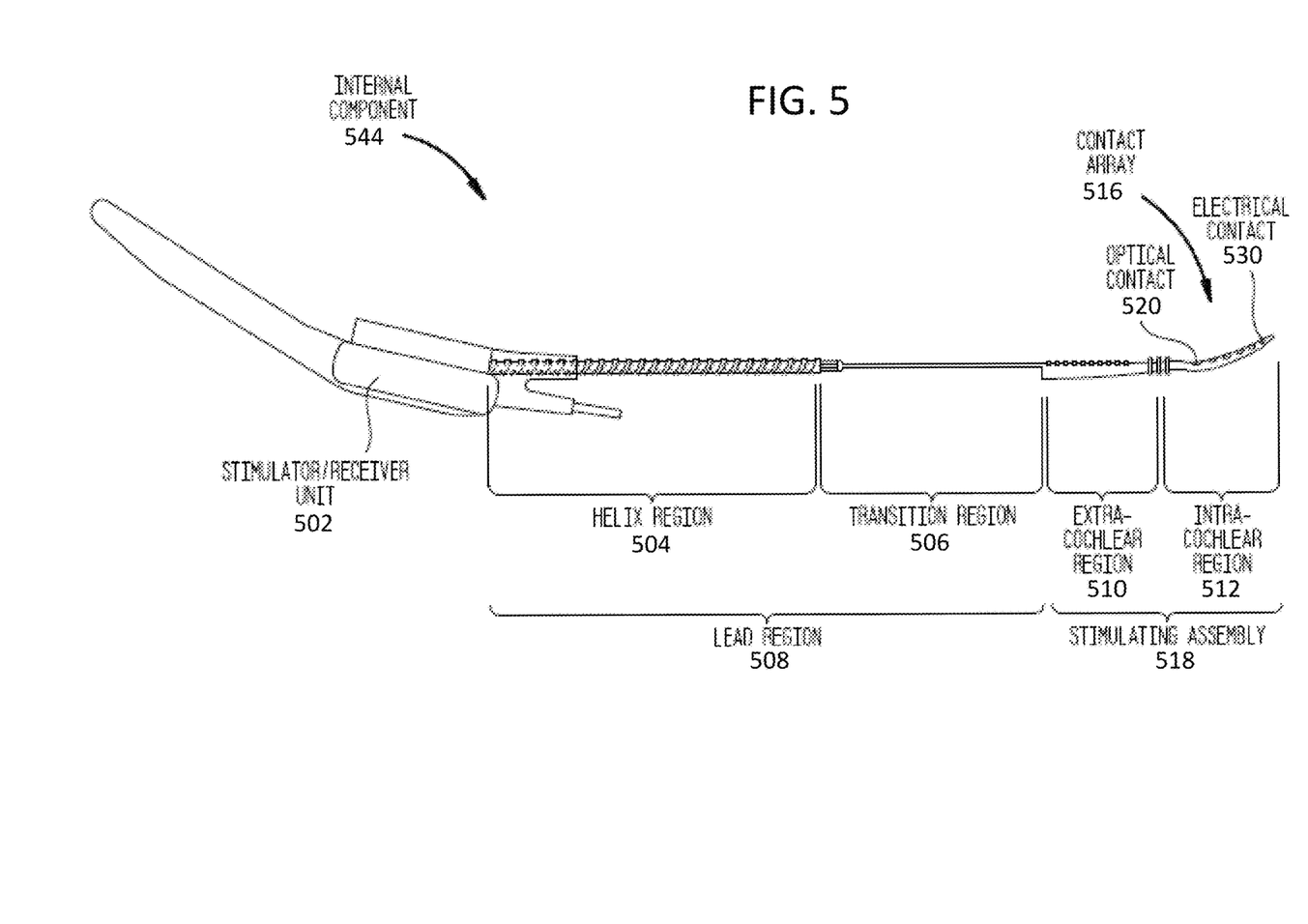
FIG. 5 is a side view of an internal component of a cochlear implant.

FIG. 5 is a side view of an internal component 544 of a cochlear implant. The internal component 544 has a stimulator/receiver unit 502 that receives encoded signals from an external component of the cochlear implant. Internal component 544 terminates in a stimulating assembly 518 that comprises an extra-cochlear region 510 and an intra-cochlear region 512. Intra-cochlear region 512 is configured to be implanted in the recipient's cochlea and has disposed thereon a contact array 516. In the present example, contact array 516 comprises both optical contacts 520 and electrical contacts 530. Present commercial devices offered by the industry use electrical contacts, research has identified the potential uses of optical stimulation alone or in conjunction with electrical or other stimulation mechanisms.

Internal component 544 further comprises a lead region 508 coupling stimulator/receiver unit 502 to stimulating assembly 518. Lead region 508 comprises a region 504 which is commonly referred to as a helix region, however, the required property is that the lead accommodate movement and is flexible, it does not need to be formed from wire wound helically. Lead region also comprises a transition region 106 which connects helix region 504 to stimulating assembly 518. As described below, optical and/or electrical stimulation signals generated by stimulator/receiver unit 502 are delivered to contact array 116 via lead region 508. Helix region 504 prevents lead region 508 and its connection to stimulator/receiver 502 and stimulating assembly 518 from being damaged due to movement of internal component 444 (or part of 444) which can occur, for example, during mastication.

Figure 6:
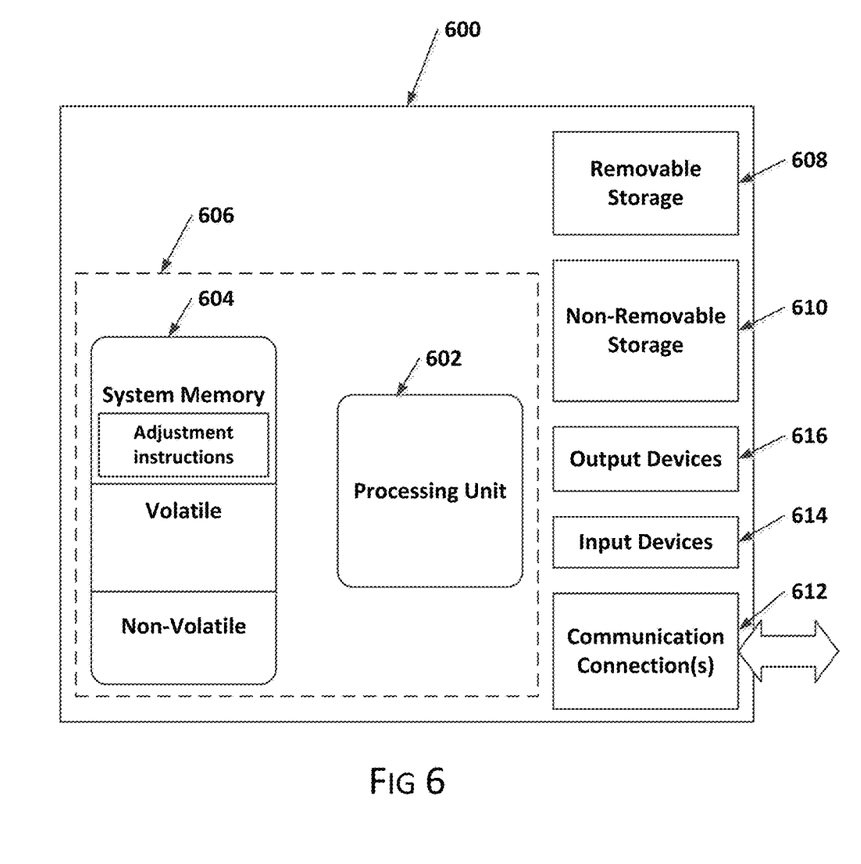
FIG. 6 illustrates one example of a suitable operating environment in which one or more of the present examples can be implemented.

FIG. 6 illustrates one example of a suitable operating environment 600 in which one or more of the present embodiments can be implemented. This is only one example of a suitable operating environment and is not intended to suggest any limitation as to the scope of use or functionality. Other well-known computing systems, environments, and/or configurations that can be suitable for use include, but are not limited to, personal computers, server computers, handheld or laptop devices, multiprocessor systems, microprocessor-based systems, programmable consumer electronics such as smart phones, network PCs, minicomputers, mainframe computers, tablets, distributed computing environments that include any of the above systems or devices, and the like. In embodiments, an auditory prosthesis includes a processing unit and memory, such as processing unit 606 and memory 604. As such, the basic configuration 606 is part of an auditory prosthesis and/or another device working in conjunction with the auditory prosthesis.

In its most basic configuration, operating environment 600 typically includes at least one processing unit 602 and memory 604. Depending on the exact configuration and type of computing device, memory 604 (storing, among other things, instructions to implement and/or perform the modules and methods disclosed herein) can be volatile (such as RAM), non-volatile (such as ROM, flash memory, etc.), or some combination of the two. This most basic configuration is illustrated in FIG. 6 by dashed line 606. Further, environment 600 can also include storage devices (removable, 608, and/or non-removable, 610) including, but not limited to, magnetic or optical disks or tape. Similarly, environment 600 can also have input device(s) 614 such as touch screens, keyboard, mouse, pen, voice input, etc. and/or output device(s) 616 such as a display, speakers, printer, etc. Also included in the environment can be one or more communication connections, 612, such as LAN, WAN, point to point, Bluetooth, RF, etc.

Operating environment 600 typically includes at least some form of computer readable media. Computer readable media can be any available media that can be accessed by processing unit 602 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible or non-transitory medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 600 can be a single device operating in a networked environment using logical connections to one or more remote devices. The remote device can be an auditory prosthesis, a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by operating environment 600 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 600 is part of a network that stores data in remote storage media for use by the computer system 600.

Figure 7:
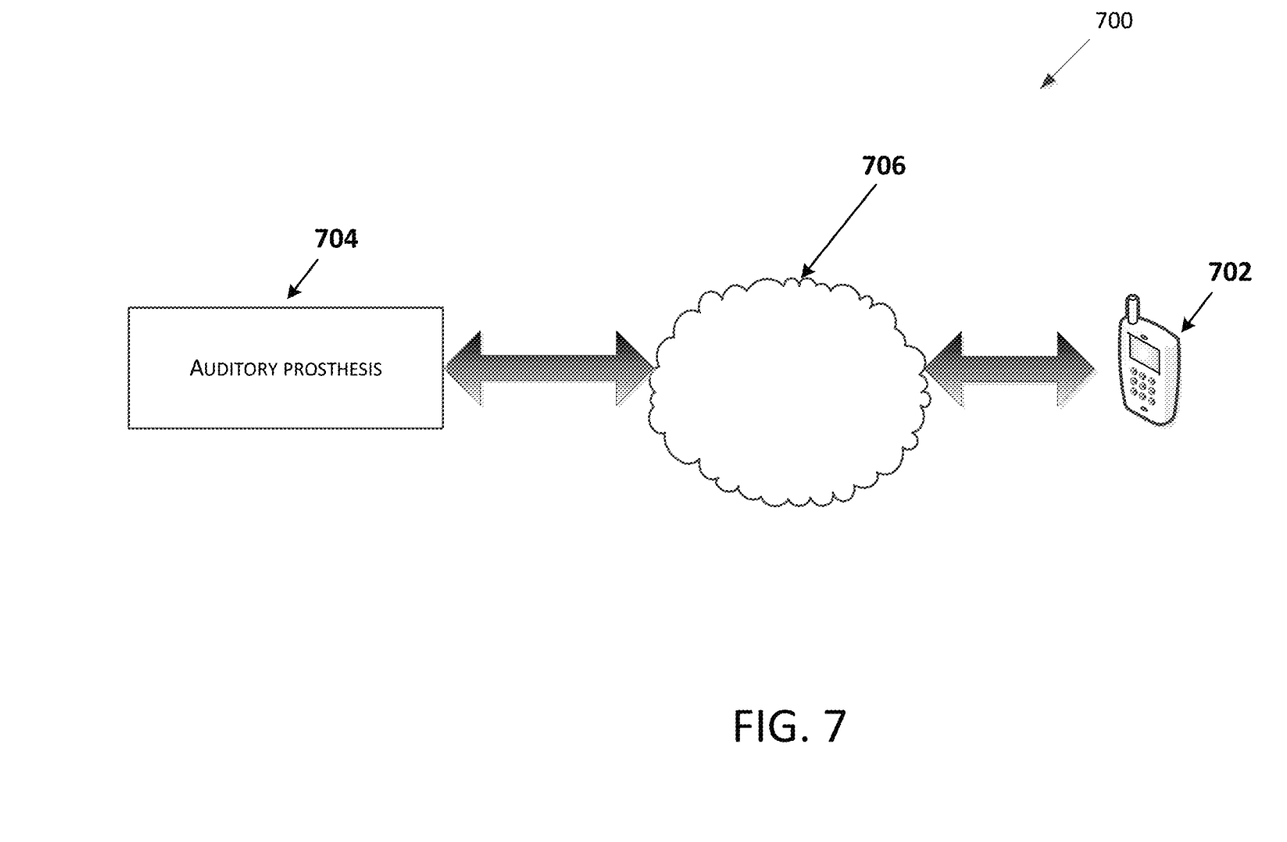
FIG. 7 is an embodiment of a network in which the various systems and methods disclosed herein can operate.

FIG. 7 is an embodiment of a system 700 in which the various systems and methods disclosed herein can operate. In embodiments, a client device, such as client device 702, can communicate with one or more auditory prostheses, such as auditory prosthesis 704, via a network 806. In embodiments, a client device can be a laptop, a personal computer, a smart phone, a PDA, a netbook, a tablet computer, a server or any other type of computing device, such as the computing device in FIG. 7. In embodiments, the client device 702 and the auditory prosthesis 704 may communicate via communication channel 706. Communication channel 706 can be any type of network capable of facilitating communications between the client device 702 and the auditory prosthesis 704. Examples of a communication channel can be an RF connection, a Bluetooth connection, a WiFi connection, or any other type of connection capable of transmitting instructions between client device 702 and auditory prosthesis 704.

In embodiments, the various systems and methods disclosed herein can be performed by an auditory prosthesis, e.g., auditory prosthesis 704, a client device, e.g., client device 702, or by both the auditory prosthesis and client device. For example, in embodiments the client device may perform a method to identify a control expression and instruct the auditory prosthesis to apply an audio setting adjustment. In such embodiments, client device 702 can transmit instructions to the auditory prosthesis to apply an audio setting instruction via communication connection 706.

Communication channel 706, in certain embodiments, is capable of real-time or otherwise suitably fast transmission of, e.g., instructions from client device 702 to auditory prosthesis 704. In such embodiments, instructions from the client device 702 based on its processing of a control expression and related conversation is received in good time by the auditory prosthesis 704. If, for instance, such instructions are not transmitted suitably fast, an audio setting adjustment to auditory prosthesis 704 might not be made in time benefit the recipient (e.g., in time for the repeat of a conversation fragment the recipient requested with the control expression).

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. A computer-implemented method comprising:
   analyzing, with at least one processing unit, a conversation between at least two parties;
   identifying a first control expression in the conversation;
   upon identifying the first control expression, determining a first setting adjustment; and
   applying the first setting adjustment to an auditory prosthesis.

2. The method of claim 1, wherein the first control expression is identified based at least in part upon tone.

3. The method of claim 1, wherein identifying the first control expression comprises:
   detecting a start time of a phrase;
   detecting an end time of the phrase; and
   determining a length of the phrase, wherein identification of the first control expression is based at least in part on the length of the phrase.

4. The method of claim 1, wherein identification of the first control expression comprises comparing at least a portion of the conversation to a dictionary.

5. The method of claim 1, wherein the first setting adjustment is selected from a hierarchy of setting adjustments.

6. The method of claim 1, wherein applying the first setting adjustment comprises sending an instruction to the auditory prosthesis.

7. The method of claim 1, wherein identification of the first control expression further comprises determining that the first control expression is spoken by a recipient of the auditory prosthesis.

8. The method of claim 7, further comprising:
   receiving a second control expression from the recipient;
   upon receiving the second control expression, determining a second setting adjustment; and
   applying the second setting adjustment to the auditory prosthesis.

9. The method of claim 1, wherein the determining the first setting adjustment is based at least in part on an environmental condition.

10. The method of claim 9, wherein the environmental condition comprises an audio input discrete from the conversation.

11. The method of claim 9, further comprising:
    detecting a change in the environmental condition; and
    upon detecting the change, reverting to a previous setting.

12. The method of claim 11, wherein the change comprises at least one of an absence of the conversation and an absence of a detected audio input discrete from the conversation.

13. The method of claim 1, wherein the first setting adjustment is selected from a plurality of setting adjustments, and wherein the plurality of setting adjustments are arranged in a hierarchy.

14. A computer storage medium encoding computer executable instructions that, when executed by at least one processor, performs a method comprising:
    analyzing a conversation;
    identifying a control expression in the conversation;
    upon identifying the control expression, determining whether the control expression was spoken by a recipient of an auditory prosthesis;
    when the control expression is spoken by the recipient, determining at least one auditory prosthesis setting; and
    applying the at least one auditory prosthesis setting to the auditory prosthesis.

15. The computer storage medium of claim 14, wherein identifying a control expression comprises accessing a dictionary of words and phrases commonly used in conversation.

16. A computer-implemented method comprising:
    receiving, with at least one processing unit, a plurality of audio inputs from a plurality of discrete sources, wherein one of the plurality of discrete sources is a recipient of an auditory prosthesis;

identifying at least one of the plurality of audio inputs as a first control expression spoken by the recipient;

upon identifying the first control expression, determining a first setting adjustment; and applying the first setting adjustment to the auditory prosthesis.

17. The method of claim 16, further comprising:

identifying at least one of the plurality of audio inputs as an environmental stimulus;

associating the environmental stimulus with the first control expression;

detecting an absence of the environmental stimulus; and upon detecting the absence, reverting to a previous setting.

18. The method of claim 16, further comprising:

identifying at least one of the plurality of audio inputs as a second control expression spoken by the recipient;

upon identifying the second control expression, determining a second setting adjustment; and applying the second setting adjustment to the auditory prosthesis.

19. The method of claim 18, wherein the second setting adjustment is selected from a hierarchy of setting adjustments.

20. The method of claim 16, further comprising:

identifying at least one of the plurality of audio inputs as a second control expression spoken by the recipient;

upon identifying the second control expression, storing the first setting adjustment.

\* \* \* \* \*